United States Patent [19]
Takagi

[11] Patent Number: 5,936,706
[45] Date of Patent: Aug. 10, 1999

[54] OPHTHALMIC INSTRUMENT

[75] Inventor: Akinari Takagi, Tokyo, Japan

[73] Assignee: Kabushiki Kaisha Topcon, Tokyo, Japan

[21] Appl. No.: 09/137,149

[22] Filed: Aug. 20, 1998

[30] Foreign Application Priority Data

Aug. 21, 1997 [JP] Japan .................................. 9-224577

[51] Int. Cl.$^6$ ...................................................... A61B 3/14
[52] U.S. Cl. ................................................................ 351/208
[58] Field of Search .................................. 351/204, 205, 351/208, 211, 212, 221, 246

[56] References Cited

U.S. PATENT DOCUMENTS

| | | |
|---|---|---|
| 5,436,679 | 7/1995 | Ohtsuka et al. . |
| 5,625,428 | 4/1997 | Isogai ....................... 351/208 |
| 5,644,375 | 7/1997 | Suzuki ...................... 351/208 |
| 5,696,573 | 12/1997 | Miwa ........................ 351/208 |

FOREIGN PATENT DOCUMENTS

5-146410  6/1993  Japan .

*Primary Examiner*—George Manuel
*Attorney, Agent, or Firm*—Finnegan, Henderson, Farabow, Garrett & Dunner, L.L.P.

[57] ABSTRACT

Disclosed herein is an ophthalmic instrument equipped with an optical alignment system. The optical alignment system has a Z-alignment index projection light system (60) which projects index light onto the cornea (C) of a subject eye (E) and a sensor (73) which receives reflected light of the index light reflected at the cornea (C). The ophthalmic instrument is further equipped with a Z-alignment detection circuit (74) which computes a positional relation between an index image formed on a light receiving surface of the sensor (73) and the cornea (C). When the result of computation by the detection circuit (74) is within a predetermined range, the subject eye is measured. The Z-alignment index projection light system (60) is provided with an aperture diaphragm (63) which has a transmittance distribution characteristic in which a quantity of light is gradually reduced from the optical axis of the system (60) in a radial direction.

6 Claims, 8 Drawing Sheets

OPHTHALMIC INSTRUMENT

BACKGROUND OF THE INVENTION

1. Field of the Invention

The present invention relates to ophthalmic instruments, such as a non-contact type ophthalmotonometer, a keratometer, a refractometer, and a cornea endothelium camera, which need to align the main body with a subject eye to be tested.

2. Description of the Related Art

There is a conventional ophthalmic equipment provided with an index projection system and a light receiving system, as described in Japan Patent Publication No. H05-146410. The index projection system projects a collimated light beam onto the cornea of a subject eye in an oblique direction. The light receiving system has a light receiving element, such as a one-dimensional PSD (Position Sensing Detector), which receives the light beam reflected in an oblique direction symmetrical with the projection direction of the index projection light system with respect to the axis of the subject eye. Based on the position at which this light receiving element received the light beam, the ophthalmic equipment performs alignment in a Z direction.

Figure 9A:
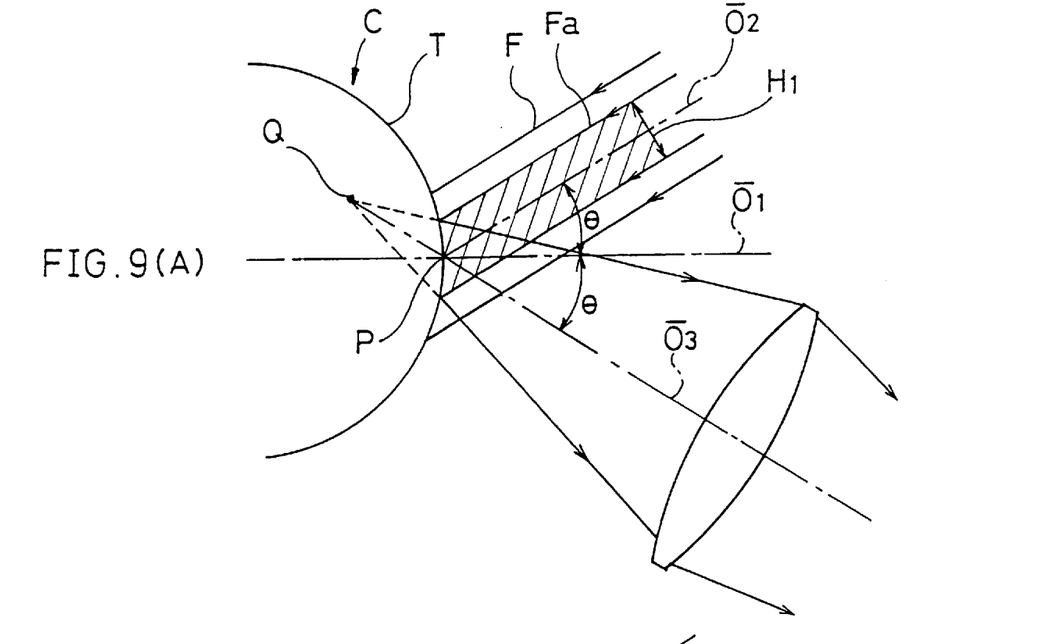
FIG. 9(A) is an explanatory diagram showing the width of an index light beam incident on a light receiving element when a cornea is at a reference position.
Figure 9B:
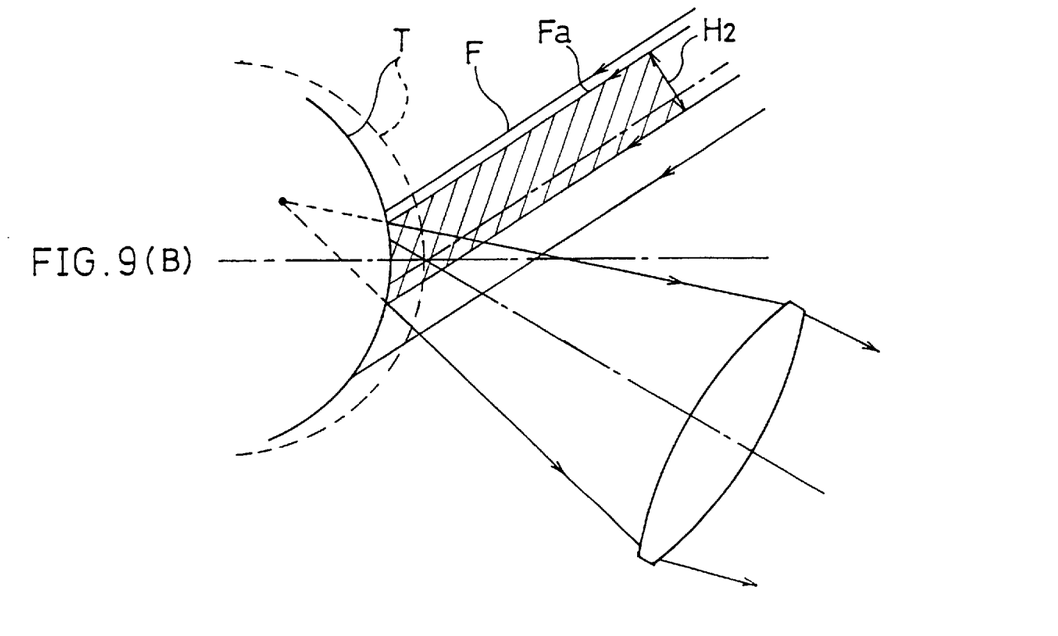
FIG. 9(B) is an explanatory diagram showing the width of the index light beam incident on the light receiving element when the cornea is shifted away from the reference position.

However, in such an ophthalmic equipment, the collimated index light has a uniform light quantity distribution. For this reason, the quantity of incident light on the light receiving element is greater in the case where the main body of the instrument is considerably shifted away from an alignment reference position than in the case where the main body is located near the alignment reference position. This is because of the spherical aberration resulting from the convex shape of the cornea surface and because the spreading angle of reflected light becomes smaller in the case where the reflected light at the outer portion of the cornea surface is employed than in the case where the reflected light at the center portion is employed. In other words, as shown in FIG. 9(A), when cornea surface T is at an alignment reference position, a portion of an index light beam F, index light beam Fa, whose width is H2, is incident on the light receiving element. On the other hand, when the cornea surface T is shifted away from the alignment reference position (indicated by a broken line), as shown in FIG. 9(B), the width of the index light beam Fa incident on the light receiving element is H2, which is greater than the width H1. Thus, if the numerical aperture (NA) in the light receiving system is constant, the light receiving efficiency of the light receiving element will become greater in the case where the cornea surface T is considerably shifted away from the alignment reference position than in the case where the cornea surface is located near the alignment reference position.

Incidentally, in the case where a one-dimensional PSD is employed, a position at which an image is formed is computed by the following equation:

$$(I1-I2)L1/(I1+I2)=L2$$

where I1 is the current output from one end of the PSD, I2 is the current output from the other end of the PSD, L1 is the length of the PSD, and L2 is the position at which an image is formed on the PSD.

In the case where a position at which an image is formed is computed with the aforementioned equation, currents I1 and I2 are converted to voltages (0 to 5 V). The voltages are converted to digital numbers (0 to 255) by an A/D converter. From the digital numbers the image formed position is computed. From this computed image formed position, the position of the cornea relative to the alignment reference position is computed.

Since the A/D converter converts an analog value between the minimum voltage 0 V and the maximum voltage 5 V to a digital value of 0 to 255, currents I1 and I2 assume a value of 0 to 255, i.e., 256 kinds of values. For this reason, the minimum resolving power is 1/512, so the detection accuracy becomes high. In other words, to obtain the minimum resolving power 1/512, the A/D converter needs to convert the maximum voltage 5 V in correspondence to 255. This is because, for example, if 3 V is converted in correspondence to 255, then voltages equal to or greater than 3 V will be all 255 and therefore detection cannot be performed. Therefore, when the cornea position is near the alignment reference position, if the value of the current (I1+I2) is set to the maximum digital value 512, the quantity of incident light on the PSD will increase as the cornea shifts away from the alignment reference position, and therefore the value of the current (I1+I2) will increase. However, even if this current increased, the converted digital value of the current will remain 512 and therefore the position of the cornea (state of alignment) cannot be detected.

Therefore, there is a need to set the A/D converter so that when the denominator (I1+I2) becomes maximum, the value is the maximum digital value 512. More specifically, when the quantity of incident light on the PSD becomes maximum, i.e., when a cornea shifts considerably away from the alignment reference position, the current (I1+I2) which is output from the terminal of the PSD must be set to the maximum digital value.

However, in the case where the maximum digital value 512 is set in the aforementioned manner, the quantity of incident light on the PSD will be reduced if a cornea is moved near the alignment reference position. Therefore, since the denominator (I1+I2) is reduced, detection accuracy decreases. In other words, there is a problem that at a position near the alignment reference position which requires high detection accuracy, the revolving power will be reduced and therefore the alignment detection accuracy will be reduced and, at a position considerably shifted away from the alignment reference position which does not require high detection accuracy, the revolving power will become high and therefore the alignment detection accuracy will become high.

SUMMARY OF THE INVENTION

An object of the present invention is to provide an ophthalmic equipment which is capable of enhancing alignment accuracy at a position near an alignment reference position.

To achieve this end, there is provided an ophthalmic instrument comprising: measurement means for measuring a subject eye; an optical alignment system having index projection means which projects an index light onto the cornea of the subject eye and light receiving means which receives reflected light of the index light reflected at the cornea; and arithmetic means for computing a positional relation between an index image formed on a light receiving surface of the light receiving means and the cornea; wherein the subject eye is measured by the measurement means when a value computed by the arithmetic means is within a predetermined range and wherein the optical alignment is provided with light quantity reducing means which has a transmittance distribution characteristic in which a quantity of light is gradually reduced from an optical axis in a radial direction.

BRIEF DESCRIPTION OF THE DRAWINGS

The above and other objects and advantages will become apparent from the following detailed description when read in conjunction with the accompanying drawings wherein.

DETAILED DESCRIPTION OF THE PREFERRED EMBODIMENT

A preferred embodiment of an ophthalmotonometer which is an ophthalmic instrument according to the present invention will hereinafter be described based on the drawings.

Figure 1:
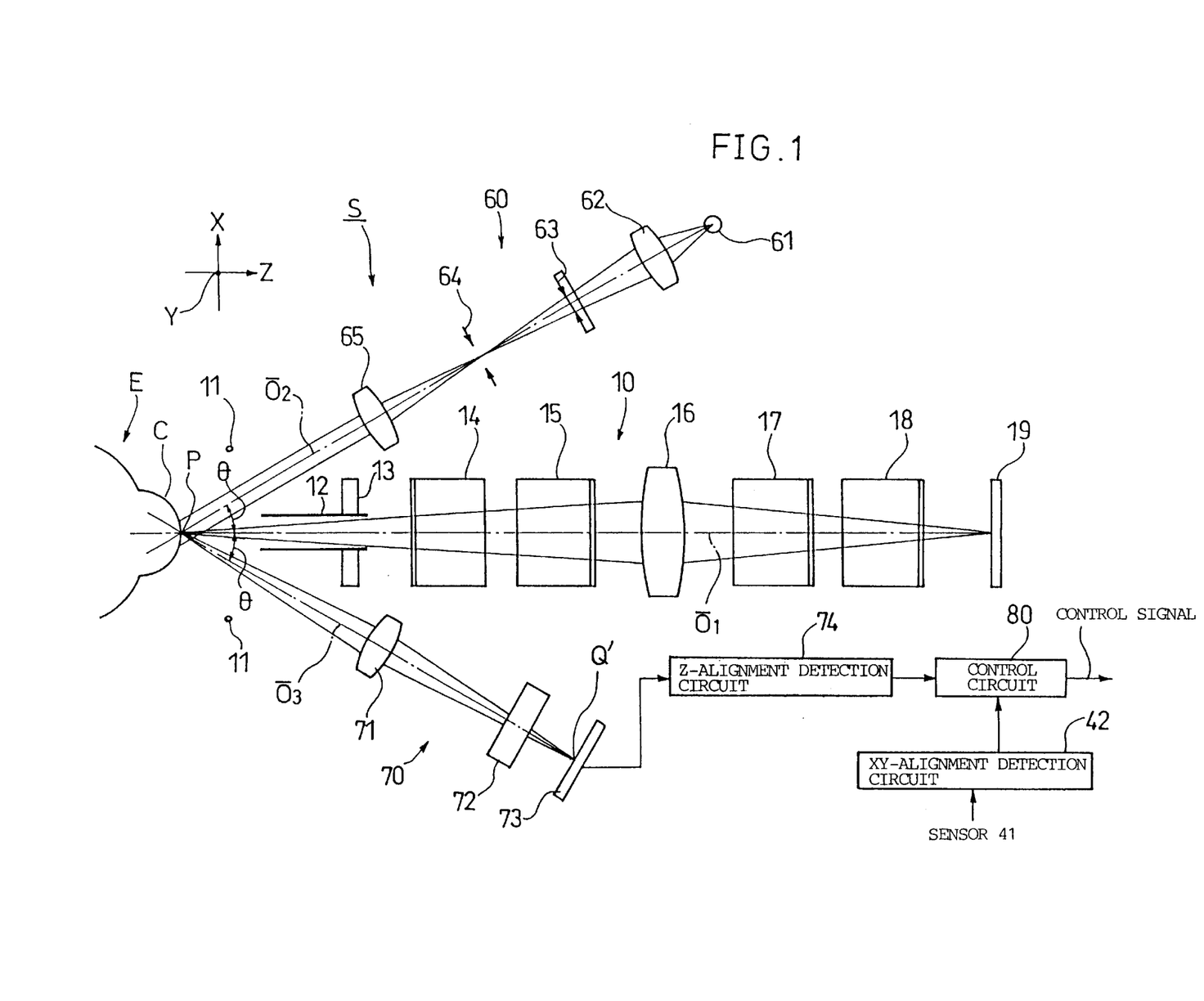
FIG. 1 is a plan view showing the optical system of an ophthalmic equipment according to the present invention.
Figure 2:
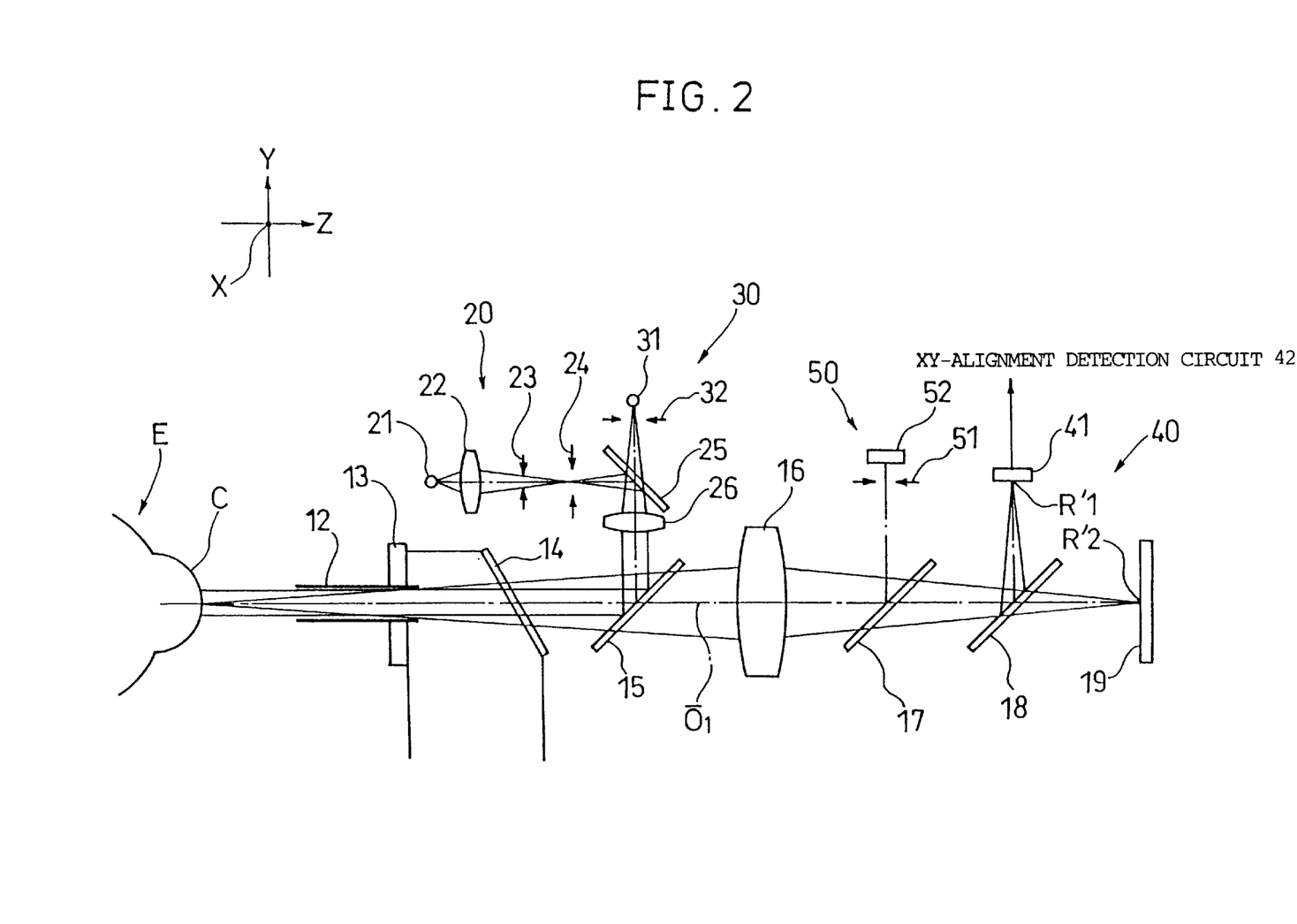
FIG. 2 is a side view showing the optical system of the ophthalmic equipment according to the present invention.

In FIGS. 1 and 2 an instrument main body S according to the present invention is equipped with a front eye portion observation system 10 which observes the front eye portion of a subject eye E, an XY-alignment index projection light system 20 which projects an index light for alignment detection and cornea deformation detection onto the cornea C of the subject eye E from the front surface, and a fixed index projection light system 30 which provides a fixed index to the subject eye E. The instrument main body S is further equipped with an XY-alignment detection light system 40 which receives the reflected light of the XY-alignment index light reflected at the cornea C and detects the positional relation in XY direction between the instrument main body S and the cornea C, a cornea deformation detection light system 50 which receives the reflected light of the XY-alignment index light reflected at the cornea C and detects the deformation quantity of the cornea C, a Z-alignment index projection light system (index projection means) 60 which projects a Z-alignment index light onto the cornea C in an oblique direction, and a Z-alignment detection light system 70 which receives the reflected light of the Z-alignment index light reflected at the cornea C in a direction symmetrical with respect to the optical axis of the front eye portion observation light system 10 and detects the positional relation in Z direction between the equipment main body S and the cornea C. The Z-alignment index projection light system 60 and the Z-alignment detection light system 70 as a whole constitute an optical alignment system.

The front eye portion observation light system 10 is equipped with a plurality of front eye portion illumination light sources 11 located to the right and left of the subject eye E to illuminate the front eye portion directly, an air spraying nozzle 12, a front eye portion window glass 13, a chamber window glass 14, a half mirror 15, an objective lens 16, half mirrors 17 and 18, and a charge coupled device (CCD) camera 19. The optical axis of the observation light system 10 is represented by O1.

The image of the front eye portion of the subject eye E, illuminated by the front eye portion illumination light source 11, passes through the inside and outside of the air spraying nozzle 12 and are transmitted through the front eye portion window glass 13, chamber window glass 14, and half mirror 15. The transmitted image is transmitted through the half mirrors 17 and 18 while being focused by the objective lens 16 and is formed onto the CCD camera 19.

The XY-alignment index projection light system 20 has an XY-alignment light source 21 for emitting infrared light, a condenser lens 22, an aperture diaphragm 23, a pinhole plate 24, a dichroic mirror 25, and a projection lens 26 arranged in an optical path so that its focal point is aligned with the pinhole plate 24. The system 20 further has the aforementioned half mirror 15, chamber window glass 14, and air spraying nozzle 12.

Figure 3:
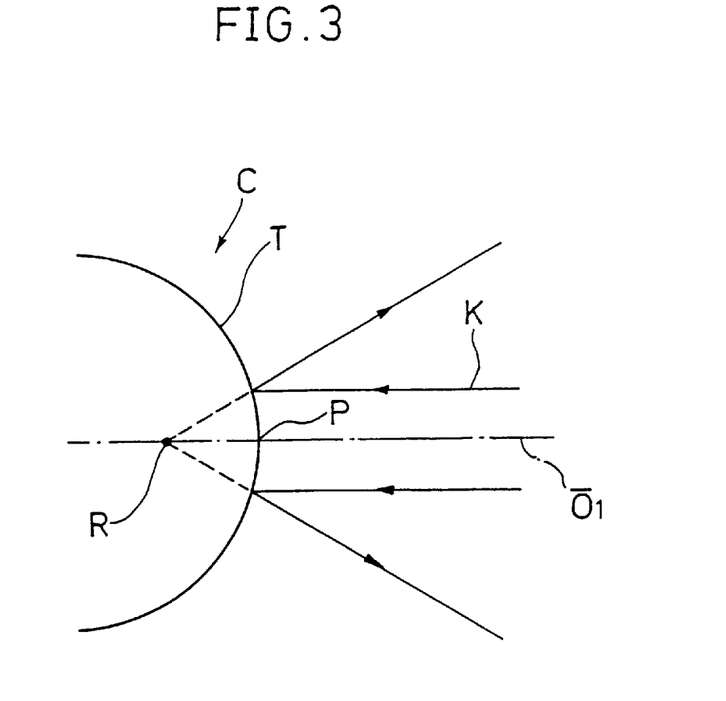
FIG. 3 is an explanatory diagram of the reflection of an alignment beam of light illuminated on a cornea from the front surface.

Infrared light emitted from the XY-alignment light source 21 passes through the aperture diaphragm 23 while being focused by the condenser lens 22, and is guided to the pinhole plate 24. Then, the beam of light, passed through the pinhole plate 24, is reflected by the dichroic mirror 25 and is collimated by the projection lens 26. After the collimated light beam has been reflected by the half mirror 15, it is transmitted through the chamber window glass 14 and passes through the inside of the air spraying nozzle 12. Finally, the light beam forms XY-alignment index light K as shown in FIG. 3. In the figure the XY-alignment index light K is reflected at the cornea surface T so that a bright-point image R is formed at the intermediate point between the vertex P of the cornea C and the center of curvature of the cornea C. Note that the aperture diaphragm 23 is provided at a position conjugate with the vertex P of the cornea C with respect to the projection lens 26.

The fixed index light system 30 has a fixed index light source 31 for emitting visible light and a pinhole plate 32. The fixed index light system 30 further has the aforementioned dichroic mirror 25, projection lens 26, half mirror 15, chamber window glass 14, and air spraying nozzle 12.

The fixed index light emitted from the fixed index light source 31 passes through the pinhole plate 32 and the dichroic mirror 25 and is collimated by the projection lens 26. After the collimated light beam has been reflected by the half mirror 15, it is transmitted through the chamber window glass 14. The transmitted light beam passes through the inside of the air spraying nozzle 12 and is guided to the subject eye E. The testee gazes steadily at the fixed index as a fixed target, whereby a line of sight is locked.

The XY-alignment detection light system 40 has the aforementioned air spraying nozzle 12, chamber window glass 14, half mirror 15, objective lens 16, and half mirrors 17 and 18. The XY-alignment detection light system 40 further has a sensor 41 and an XY-alignment detection circuit 42.

The reflected light beam, projected on the cornea C and reflected at the cornea surface T by the XY-alignment index projection light system 20, passes through the inside of the nozzle 12 and is transmitted through the chamber window glass 14 and the half mirror 15. The transmitted light is partially transmitted through the half mirror 17 while being focused by the objective lens 16, and a portion of the light transmitted through the half mirror 17 is reflected at the half mirror 18. The light beam, reflected at the half mirror 18, forms a bright-point image R'1 onto the sensor 41. The sensor 41 is a light receiving sensor which can detect position, such as a PSD. The XY-alignment detection circuit 42 computes the positional relation (XY direction) between the instrument main body S and the cornea C by a known means on the basis of the output of the sensor 41, and outputs the result of computation to a control circuit 80.

Figure 4:
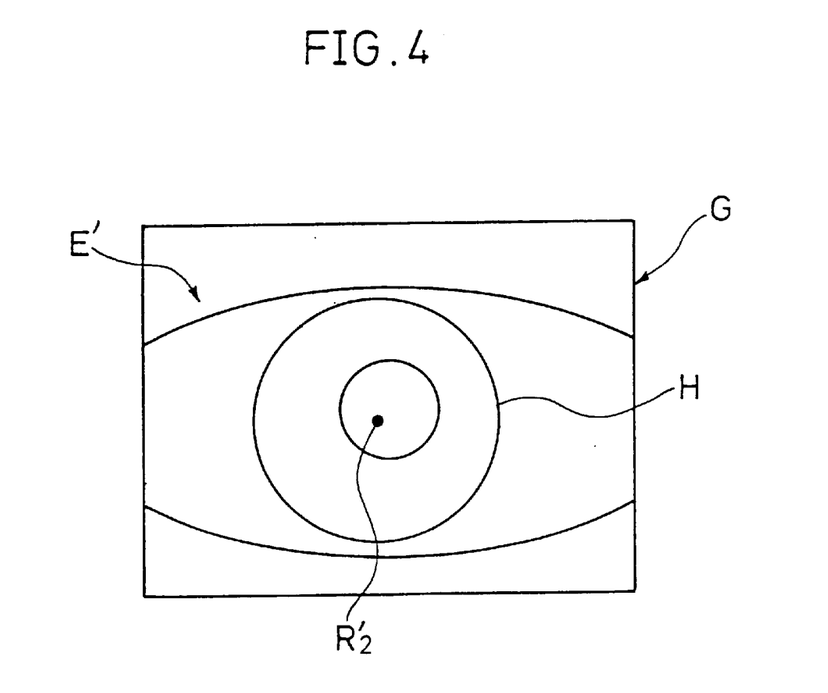
FIG. 4 is an explanatory diagram showing the image of the front eye portion displayed on the screen of a monitor.

On the other hand, the light beam, reflected at the cornea C and transmitted through the half mirror 18, forms a bright-point image R'2 onto the CCD camera 19. The CCD camera 19 outputs an image signal to a monitor, and as shown in FIG. 4, the front eye portion image E' of the subject eye E and the bright-point image R'2 of the XY-alignment index light are displayed on the screen G of the monitor. In FIG. 4, reference character H denotes an alignment auxiliary mark generated by image generating means (not shown).

Furthermore, the partial light beam reflected by the half mirror 17 is guided to the cornea deformation detection light system 50. The light beam passes through a pinhole plate 51 and is guided to a sensor 52. The sensor 52 is a light receiving sensor which can detect a quantity of light, such as a photodiode.

The Z-alignment index projection light system 60 has a Z-alignment light source 61 for emitting infrared light, a condenser lens 62, an aperture diaphragm 63, a pinhole plate 64, and a projection lens 65 arranged in an optical path so that its focal point is aligned with the pinhole plate 64. The optical axis of this system 60 is represented by O2.

Figure 5:
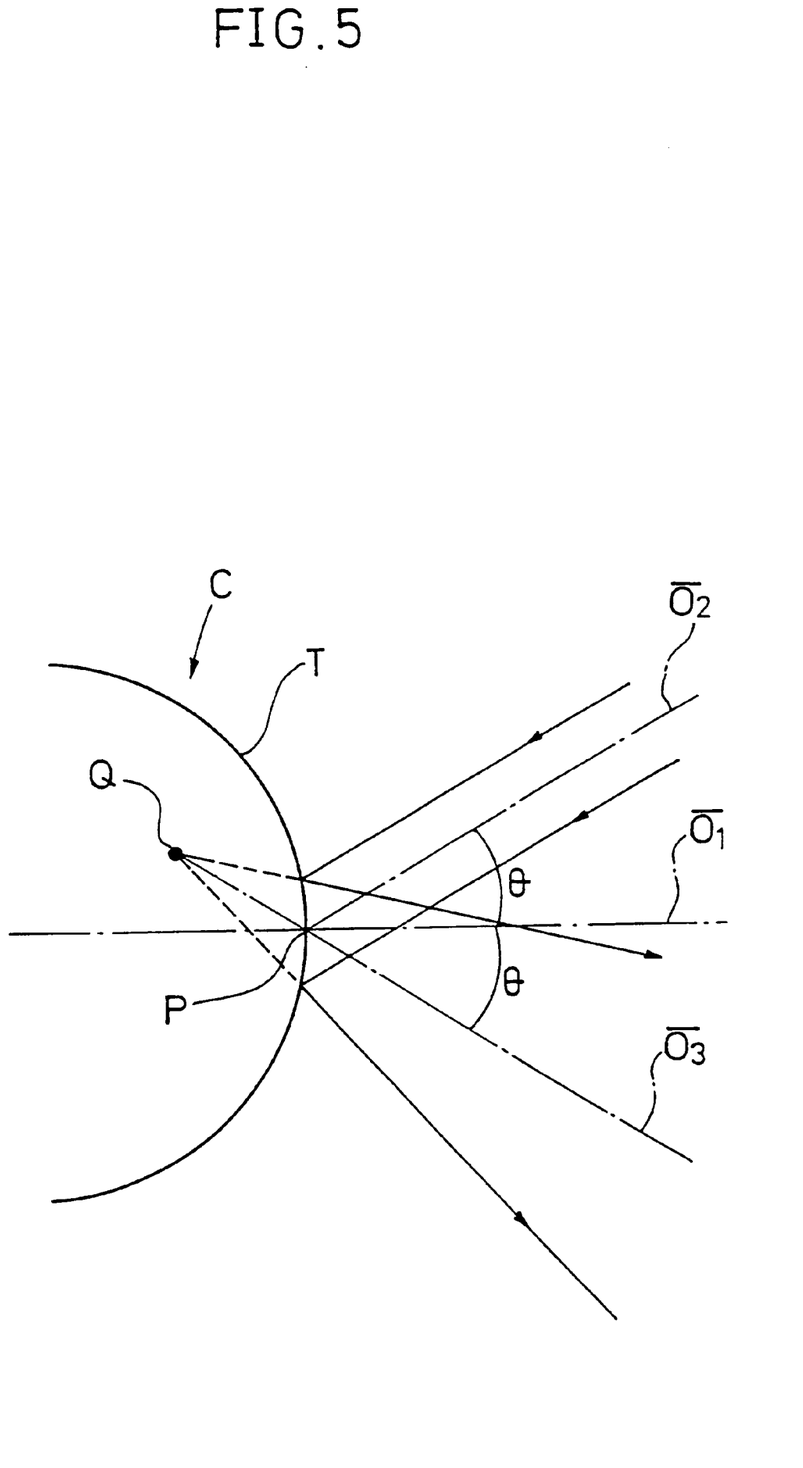
FIG. 5 is an explanatory diagram of the reflection of an alignment beam of light illuminated on the cornea in an oblique direction.

Infrared light emitted from the Z-alignment light source 61 passes through the aperture diaphragm 63 while being focused by the condenser lens 62, and is guided to the pinhole plate 64. The light beam transmitted through the pinhole plate 64 is collimated by the projection lens 65. The collimated light beam (index light) F is guided to the cornea C. As shown in FIG. 5, the collimated light beam F is reflected at the cornea surface T so that it forms a bright-point image Q. Note that the aperture diaphragm 63 is provided at a position conjugate with the vertex P of the cornea C with respect to the projection lens 65.

Figure 6A:
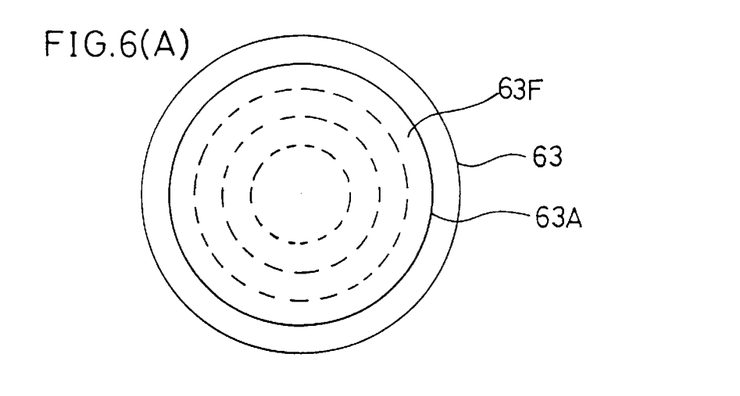
FIG. 6(A) is a plan view showing an aperture diaphragm.

The opening 63A of this aperture diaphragm 63 is provided with a filter 63F having a transmittance distribution characteristic in which its transmittance is gradually reduced from the center toward the radially outer portion, as shown in FIGS. 6(A) and (B). With this filter 63F, the light quantity of the collimated light beam F shown in FIG. 5 is gradually reduced from the optical axis O2 toward the radially outer portion, as shown in FIG. 6(C).

The Z-alignment detection light system 70 has an image forming lens 71, a cylindrical lens 72 having power in a Y direction, and a sensor (light receiving means) 73. The optical axis of this system 70 is represented by O3.

The index light F projected by the Z-alignment index projection light system 60 is reflected at the cornea surface T. The reflected light forms a bright-point image Q' onto the sensor 73 through the cylindrical lens 72 while being focused by the image forming lens 71. The sensor 73 is a light receiving sensor which can detect position, such as a line sensor or a PSD. Information from the sensor 73 is guided to the Z-alignment detection circuit (arithmetic means) 74.

The Z-alignment detection circuit 74 computes the positional relation in Z direction between the instrument main body S and the cornea C by a known means, and outputs the result of computation to the control circuit 80.

Figure 6B:
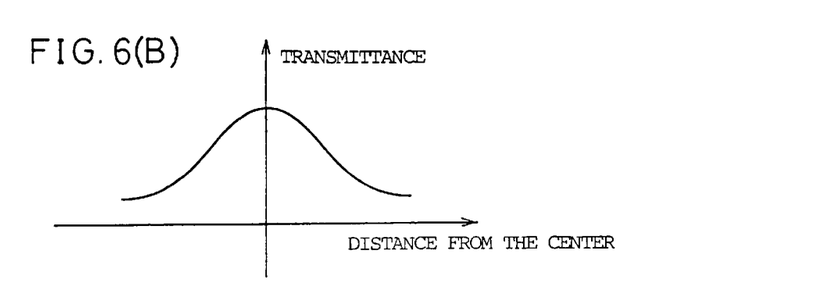
FIG. 6(B) is a graph showing the transmittance distribution characteristic of the aperture diaphragm.
Figure 6C:
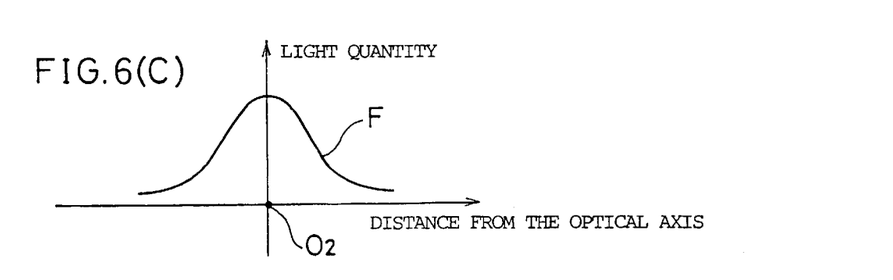
FIG. 6(C) is a graph showing the light quantity distribution of an index light.
Figure 6D:
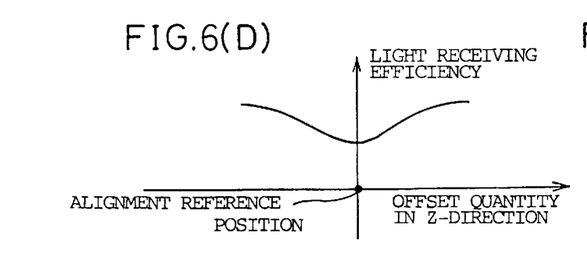
FIG. 6(D) is a graph showing the light receiving efficiency of a sensor relative to an offset quantity of a cornea from an alignment reference position.
Figure 6E:
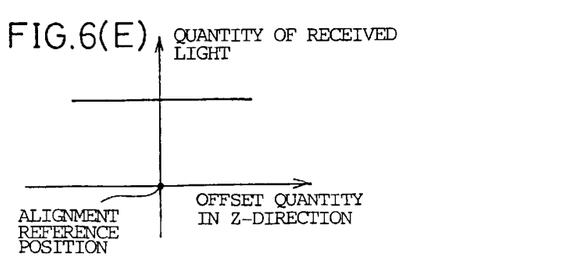
FIG. 6(E) is a graph showing the quantity of light received by the sensor relative to an offset quantity of a cornea from an alignment reference position.

Incidentally, if the cornea C shifts away from the alignment reference position (shown in FIG. 5), the light receiving efficiency of the sensor 73 will increase as shown in FIG. 6(D). However, as shown in FIG. 6(C), the light quantity of the index light F is gradually reduced from the optical axis O2 in a radially outer direction. Therefore, as shown in FIG. 6(E), the quantity of light that is received by the sensor 73 can be made constant regardless of the offset quantity of the cornea C from the alignment reference position.

For this reason, alignment accuracy near the alignment reference position can be enhanced, so that measurement accuracy can be enhanced.

On the XZ plane, the bright-point image Q and the sensor 73 are in a relation of conjugate position with respect to the image forming lens 71. On the YZ plane, the vertex P of the cornea C and the sensor 73 are in a relation of conjugate position with respect to the image forming lens 71 and cylindrical lens 72. In other words, the sensor 73 and the aperture diaphragm 63 are in a conjugate relation (the magnification at this time is selected so that the image of the aperture diaphragm 63 becomes smaller than the size of the sensor 73). Therefore, even if the cornea C were shifted in the Y direction, the reflected light at the cornea surface T will be efficiently incident on the sensor 73. Also, if a long slit light is projected in the Y direction, the efficiency will be reduced, but the same effect can be obtained.

The tester moves the instrument main body S in X, Y, and Z directions manually so that the bright-point image R2' is located within the alignment auxiliary mark H and also they are in focus, while observing the front eye portion image E' with the monitor screen shown in FIG. 4. In this manner, alignment is performed. At this time, if the outputs of the XY-alignment detection circuit 42 and Z-alignment detection circuit 74 are within a predetermined range, the control circuit 80 will cause the air spraying means to operate. Air is sprayed from the air spraying nozzle 12 toward the cornea C, and the deformation of the cornea C at that time is detected by the cornea deformation detection system 50. When the deformation of the cornea C reaches a predetermined deformation, the intraocular pressure of the subject eye E is computed from the air spraying pressure. The cornea deformation detection system 50, etc., constitute measurement means which measures the intraocular pressure of the subject eye E.

Note that, based on the XY-alignment information output from the XY-alignment detection circuit 42 and the Z-alignment information output from the X-alignment detection circuit 74, the state of alignment between the main body S and the subject eye E may be detected. The result of detection may be displayed on a CRT, etc.

Figure 7:
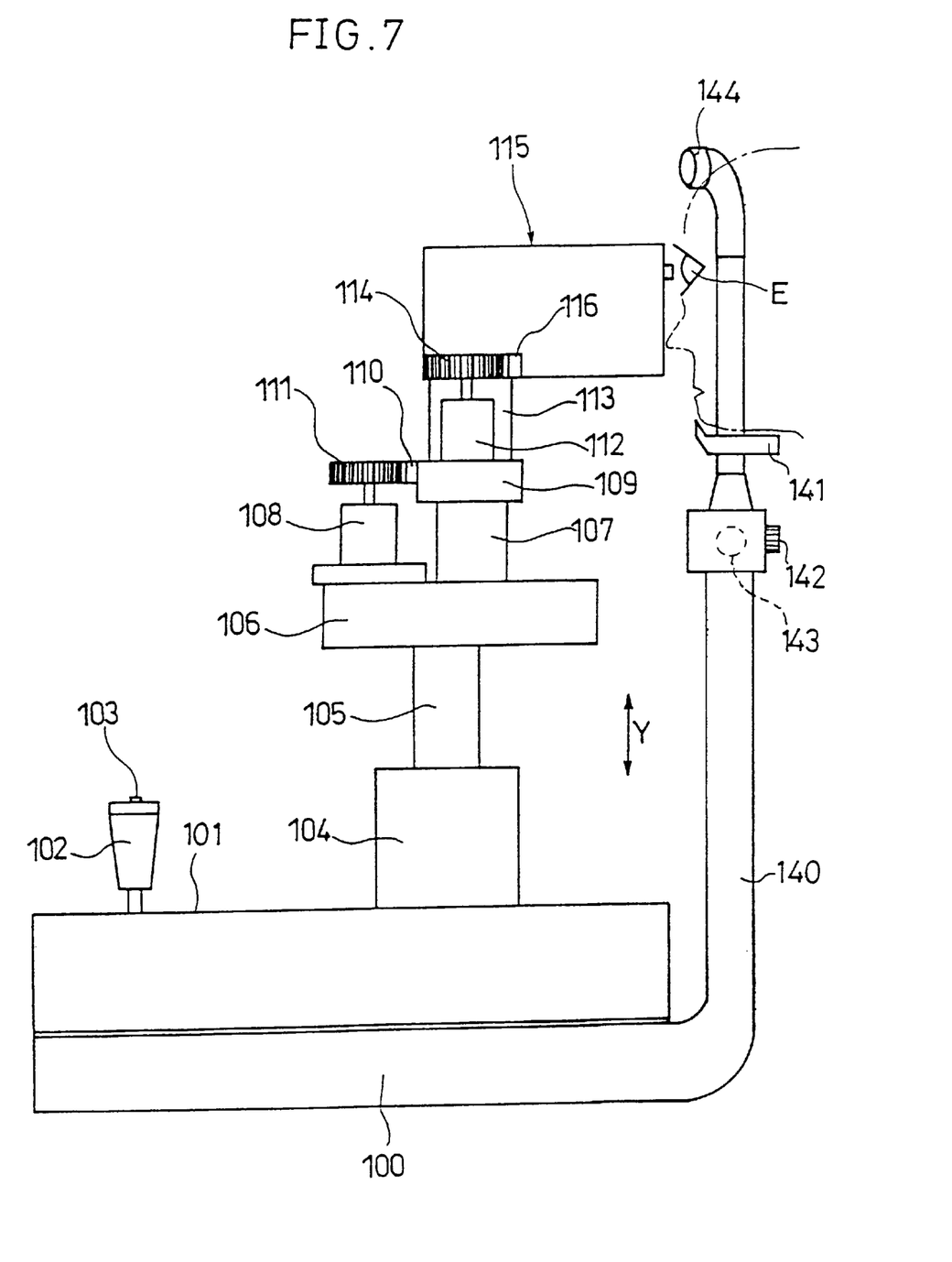
FIG. 7 is a side view of the ophthalmic equipment according to the present invention.

FIG. 7 illustrates an ophthalmotonometer constructed in accordance with the present invention. In the figure, reference numeral 100 denotes a base incorporated with a power supply (not shown). A support table 101 is provided on the upper portion of the base 100 so that it is movable in back-and-forth and right-and-left directions by a control lever 102. The control lever 102 is provided with a manual switch 103. This manual switch 103 is employed in a manual mode. A motor 104 and a column 105 are provided on the upper portion of the support table 101.

A column 140 is attached to the right portion of the base 100. This column 140 is provided with a chin receiver 141. This chin receiver 141 is moved in an up-and-down direction (Y direction) by an adjusting knob 142 and in a right-and-left direction (X direction) by an adjusting knob 143. Reference numeral 144 denotes a forehead pad.

The motor 104 and column 105 are coupled together by a pinion and a rack (not shown) so that the column 105 can be moved in the up-and-down direction (Y direction) by the motor 104. A table 106 is mounted on the upper end of the column 105.

Figure 8:
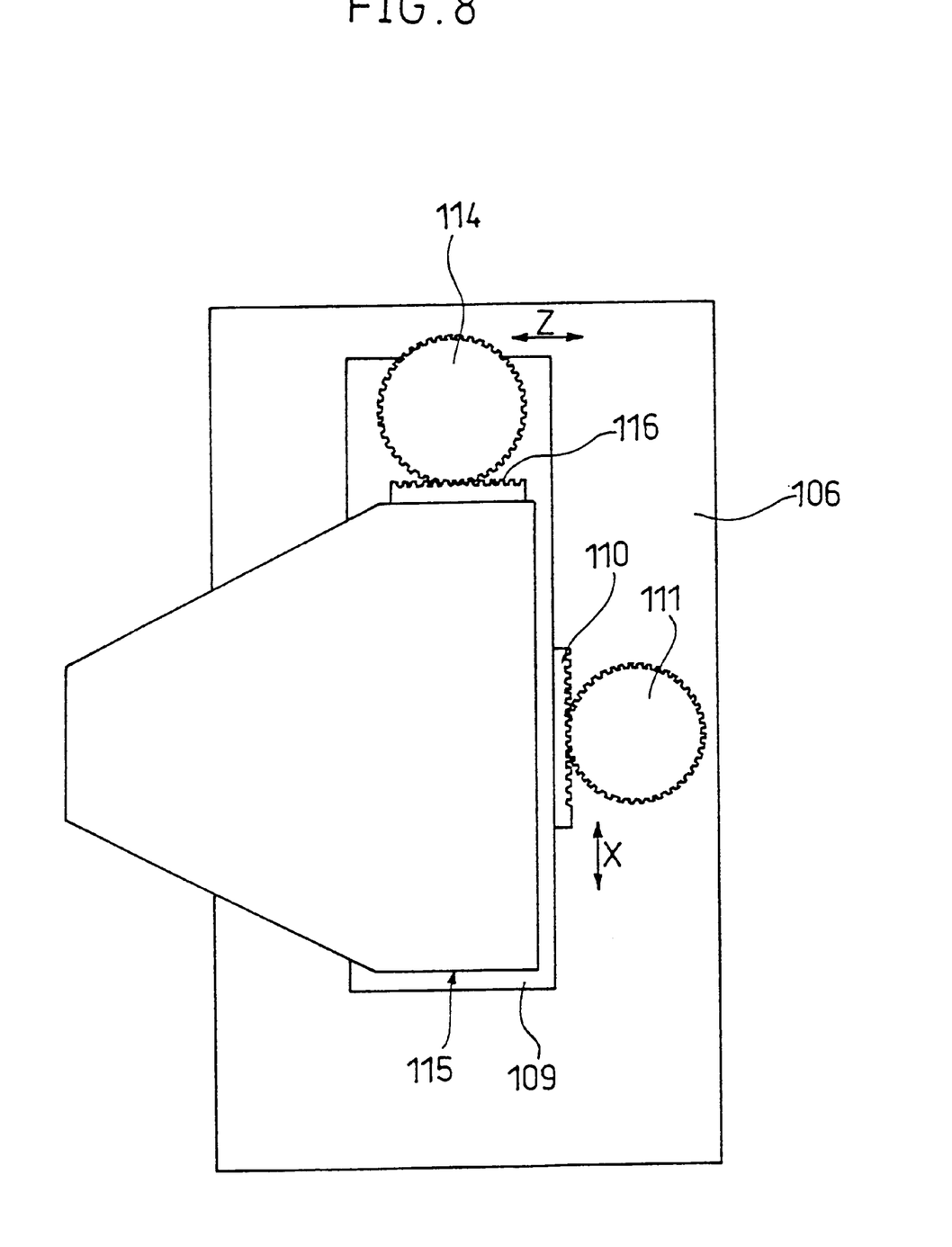
FIG. 8 is a plan view showing the essential part of the ophthalmic equipment according to the present invention.

The table 106 is provided with a column 107 and a motor 108. The upper end of the column 107 is provided with a slidable table 109. The rear end of the table 109 is provided with a rack 110, as shown in FIG. 8. The output shaft of the motor 108 is provided with a pinion 111, which in turn meshes with the rack 110. Also, the upper portion of the table 109 is provided with a motor 112 and a column 113. The output shaft of the motor 112 is provided with a pinion 114. Furthermore, a main body casing 115 is provided on the upper portion of the column 113 so as be slidable. The side portion of the main body casing 115 is provided with a rack 116. The rack 116 meshes with the pinion 114. Note that the optical systems shown in FIGS. 1 and 2 are housed interiorly of the main body casing 115.

The motors 104, 108, and 112 are controlled by a control signal which is output from the aforementioned control circuit 80. When the control signal is output to the motor 104, the main body casing 115 is adjusted in the Y direction. When the control signal is output to the motor 108, the main body casing 115 is adjusted in the X direction. Furthermore, when the control signal is output to the motor 112, the main body casing 115 is adjusted in the Z direction. In this manner, automatic alignment is performed.

In the aforementioned embodiment, although the aperture diaphragm 63 has a transmittance distribution characteristic, a filter with a transmittance distribution characteristic shown in FIG. 6(B) may be arranged directly in front of the sensor 73 instead of the aperture diaphragm 63. This filter may also be arranged in front of the projection lens 65. Furthermore, a diaphragm may be provided in front of the lens 65 to shut out a portion of a light beam which is guided to a place remote from the optical axis.

In the aforementioned embodiment, while the present invention is applied to the alignment system of the ophthalmotonometer, the invention is not limited to this but may be applied to the alignment system of a keratometer, a refractometer, a cornea endothelium camera, etc.

What is claimed is:

1. An ophthalmic instrument comprising:

measurement means for measuring a subject eye;

an optical alignment system having index projection means which projects index light onto a cornea of said subject eye and light receiving means which receives reflected light of said index light reflected at said cornea; and arithmetic means for computing a positional relation between a body of said ophthalmic instrument and said cornea, based on a position of an index image formed on a light receiving surface of said light receiving means;

wherein said optical alignment system is provided with light quantity reducing means which has a transmittance distribution characteristic in which a quantity of light is gradually reduced from an optical axis in a radial direction.

2. The ophthalmic instrument as set forth in claim 1, wherein said light quantity reducing means is provided in an optical path of said index projection means.

3. The ophthalmic instrument as set forth in claim 1, wherein said light quantity reducing means is provided in an optical path of said light receiving means.

4. The ophthalmic instrument as set forth in any one of claims 1 through 3, wherein said light quantity reducing means is a filter whose transmittance is reduced from an optical axis in a radial direction.

5. The ophthalmic instrument as set forth in claim 4, wherein said filter is provided in an aperture diaphragm of said optical alignment system.

6. The ophthalmic instrument as set forth in claim 5, wherein said aperture diaphragm and said light receiving means are in a conjugate relation.

* * * * *